(12) United States Patent
Guttag

(10) Patent No.: US 6,436,916 B1
(45) Date of Patent: Aug. 20, 2002

(54) IBUPROFEN-ASPIRIN AND HYDROXYMETHYLACYLFULVENE ANALOGS

(76) Inventor: Alvin Guttag, 7577 Central Park Blvd., Suite 316, Mason, OH (US) 45040

( * ) Notice: Subject to any disclaimer, the term of this patent is extended or adjusted under 35 U.S.C. 154(b) by 0 days.

(21) Appl. No.: 09/954,853

(22) Filed: Sep. 18, 2001

Related U.S. Application Data

(60) Provisional application No. 60/239,255, filed on Oct. 12, 2000.

(51) Int. Cl.$^7$ .............................................. A01N 37/36
(52) U.S. Cl. ...................... 514/164; 560/143; 502/400; 514/165; 514/229; 514/223; 514/224; 514/532
(58) Field of Search ..................... 560/143; 562/400; 514/164, 165, 532; 554/229, 223, 224

(56) References Cited

U.S. PATENT DOCUMENTS

| | | | |
|---|---|---|---|
| 3,220,960 A | 11/1965 | Wicterle et al. | 260/2.5 |
| 3,228,831 A | 1/1966 | Nicholson et al. | 167/53 |
| 3,385,886 A | 5/1968 | Nicholson et al. | 260/515 |
| 3,630,715 A | 12/1971 | Guttag | 71/109 |
| 4,643,995 A | 2/1987 | Engel et al. | 514/210 |
| 5,439,936 A | 8/1995 | Kelner et al. | 514/546 |
| 5,523,490 A | 6/1996 | Kelner et al. | 568/374 |
| 5,563,176 A | 10/1996 | Kelner et al. | 514/691 |
| 5,723,632 A | 3/1998 | McMorris | 549/331 |
| 5,760,261 A | 6/1998 | Guttag | 554/229 |
| 5,856,580 A | 1/1999 | McMorris | 568/347 |
| 5,910,511 A | 6/1999 | Guttag | 514/533 |
| 5,932,553 A | 8/1999 | McMorris et al. | 514/23 |
| 6,025,328 A | 2/2000 | McMorris et al. | 514/2 |
| 6,037,338 A | 3/2000 | Guttag | 514/165 |
| 6,069,283 A | 5/2000 | McMorris et al. | 568/374 |
| 6,160,184 A | 12/2000 | McMorris | 568/374 |

FOREIGN PATENT DOCUMENTS

| | | | |
|---|---|---|---|
| CZ | 158430 | | 6/1975 |
| DE | 1814607 | * | 7/1968 |
| ES | 2049647 | * | 4/1994 |
| FR | 1575571 | * | 7/1969 |
| FR | 1584915 | * | 1/1970 |
| FR | 2044356 | * | 2/1971 |

OTHER PUBLICATIONS

Dong et al, The Journal of Biological Chemistry, vol. 272, No. 15, pp. 9962–9970.*
Gilbert et al., Journal of Chemical Research, vol. 7, 1977, 172.*
CA vol. 71, No. 123843 a New derivatives of Phenylacetic acid used as antiinflammatory agents, 1969, Aries Robert.*
Arnst, "Aspirin Takes on a New Job: Fighting Colon Cancer," *Business Week*, (Jun. 15, 1998). p. 132.
Hrabak et al, *Chem. Abst.* vol. 84 p. 430 item 16972p.
Maruko Pharm. Co., *Chem Abst.*, 94, (1981), p. 544, 46974q.
Pala et al, "Terpene Compounds as Drugs: Terpenyl Derivatives of Salicylic Acid," *J. Med. Chem.*, 11:4 (1968) pp. 910–911.
Prouix, "Scientists Debate Change in Infant Formula," *The Washington Post*, Health Section, (Mar. 4, 1997), p. 19.
Reyes et al., *Chem Abst.*, 101, (1984), p. 574, 6756b.
Rovner, "Aspirin: New Tricks for an Old Drug," *The Washington Post* (Article was received incomplete only pp. 10, 12).
Zurer, "Total Synthesis Yields Anticancer Drug," Chem Eng. News, (Feb. 10, 1997), pp. 7–8.
Dong et al, The Journal of Biological Chemistry, vol. 272 pp. 9962–9970.*

* cited by examiner

*Primary Examiner*—Paul J. Killos
*Assistant Examiner*—Hector M Reyes
(74) *Attorney, Agent, or Firm*—Eric W. Guttag; Smith, Guttag, Hasse & Nesbitt Ltd

(57) ABSTRACT

Ibuprofen-aspirin compounds useful in treating aspirin or ibuprofen-treatable conditions and hydroxymethylacylfulvene analogs useful as antitumor drugs.

18 Claims, No Drawings

IBUPROFEN-ASPIRIN AND HYDROXYMETHYLACYLFULVENE ANALOGS

CROSS REFERENCE TO RELATED APPLICATIONS

This application claims the benefit of copending U.S. Provisional Patent Application Ser. No. 60/239,255, filed Oct. 12, 2000.

TECHNICAL FIELD

This invention is directed to aralkyl esters (more preferably alkaralkyl esters) of salicylic acid and their use in treating aspirin or ibuprofen-treatable conditions. This invention is also directed at hydroxymethylacylfulvene analogs and their use as antitumor drugs.

BACKGROUND OF THE INVENTION

Aspirin (acetylsalicylic acid), one of the oldest over-the-counter drugs having been marketed since 1899, continues to be used for relief from headaches, fevers and arthritis pain. Aspirin works as an analgesic to reduce pain, an anti-pyretic to reduce fever and an anti-inflammatory agent. Recently, aspirin has been shown to aid in the prevention of heart attacks. However, aspirin does have undesirable side effects. Use of aspirin has been linked to Reye's Syndrome in children, hearing impairment in heavy users, stomach problems, excessive bleeding and certain rare but serious complications of pregnancy.

Other anti-inflammatory drugs that reduce pain such as acetaminophen (under the trade name Tylenol) and ibuprofen (under the trade names Motrin, Advil and Nuprin) are also available. However, these also are associated with potentially harmful side effects. Acetaminophen, the most preferred analgesic after aspirin, can cause delayed liver damage when used excessively and major kidney damage with long-term chronic use. Accordingly, there is still a need for analgesic, anti-pyretic and anti-inflammatory drugs that can be used in place of aspirin, ibuprofen and acetaminophen.

A listing of human cancers for which chemotherapy has exerted a predominant role in increasing life span, approaching normal life expectancy, includes Burkitt's lymphoma, acute lymphocytic leukemia and Hodgkin's disease, along with about 10–15 other tumor types. See, for example, Golden et al., *Eur. J Cancer*, 12, 129 (1981) (Table 1). While the cure rate of these cancers illustrates the level of success of screening systems in selecting antitumor agents that are effective in man, these responsive tumors represent only a small fraction of the various types of cancer and, notably, there are relatively few drugs highly active against clinical solid tumors. Such drugs include cyclophosphamide, adriamycin, 5-FU, hexamethylmelamine and the like. Thus, patients with many types of malignancies remain at significant risk for relapse and mortality.

After relapse, some patients can be reinduced into remission with their initial treatment regimen. However, higher doses of the initial chemotherapeutic agent or the use of additional agents are frequently required, indicating the development of at least partial drug resistance. Recent evidence indicates drug resistance can develop simultaneously to several agents, including ones to which the patient was not exposed. The development of multiple-drug resistant (MDR) tumors may be a function of tumor mass and constitutes a major cause of treatment failure. To overcome this drug resistance, high-dose chemotherapy with or without radiation and allogenic or autologous bone marrow transplantation can be employed. The high-dose chemotherapy may employ the original drug(s) or be altered to include additional agents. The development of new drugs non-cross resistant with MDR phenotypes is required to further the curative potential of current regimens and to facilitate curative interventions in previously treated patients.

Recently, the in vitro anti-tumor activity of a novel class of natural products called illudins has been examined. See Kelner et al., *Cancer Res.*, 47, 3186 (1987). The extreme toxicity of illudins has prevented any applications in human tumor therapy. Recently, synthetic analogs of the illudins have been developed which exhibit promising antitumor activity. See, for example, U.S. Pat. No. 5,439,936 (Kelner et al), issued Aug. 8, 1995 and U.S. Pat. No. 5,523490 (Kelner et al), issued Jun. 4, 1996. These include hydroxymethylacylfluvene (HMAF) which has recently shown promise as an antitumor drug. See Zurer, *Chem. Eng. News*, page 7 (Feb. 10, 1997) However, there still exists a continuing need for chemotherapeutic agents which inhibit tumor growth, especially solid tumor growth, and which have an adequate therapeutic index to be effective for in vivo treatment.

SUMMARY OF THE INVENTION

The present invention relates to ibuprofen-aspirin compounds useful in treating various conditions previously treated with aspirin or ibuprofen and which have the formula I:

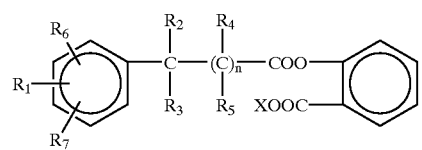

wherein $R_1$ is hydrogen, benzoyl or alkyl, e.g., lower alkyl of 1 to 6 carbon atoms, and preferably is a branched chain alkyl, e.g., isoalkyl, sec-alkyl or tert-alkyl; $R_2$ and $R_3$ are hydrogen or lower alkyl, e.g. methyl, ethyl or propyl, preferably $R_2$ is hydrogen and $R_3$ is methyl; n is zero or a small integer, e.g., 1, 2, or 3; $R_4$ and $R_5$ are hydrogen or lower alkyl, preferably hydrogen or methyl; $R_6$ and $R_7$ are as defined for $R_1$ and are preferably hydrogen; and X is hydrogen or a pharmaceutically acceptable salt forming metal or group (advantageously, the sodium, potassium, lithium, calcium or ammonium salts). When $R_1$ is alkyl, it is preferably in the para position but can be in the ortho or meta position. When $R_1$ is benzoyl, it is preferably in the meta position. An example of such a compound is the phenolic acid ester of ketoprofen(2-(3-benzoylphenyl)-propionic acid.

The present invention also relates to hydroxymethylacylfulvene analog compounds useful as antitumor drugs and which have the formula II:

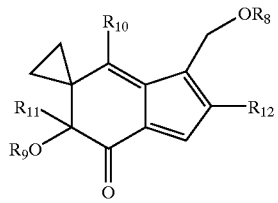

wherein $R_8$ is an acyl group of an acid having at least 3 carbon atoms, the acid being selected from alkenoic acids having 1 to 6 ethylenic double bonds, phenoxyalkanoic acids, ring halogenated phenoxyalkanoic acids having 1 to 3 ring halogen atoms, alkylidene bis-phenoxyalkanoic acids and alkylidene bis-ring halogenated phenoxyalkanoic acids having 1 to 3 ring halogen atoms in each ring; $R_9$ is hydrogen, an alkyl group having 1 to 4 carbon atoms, or an acyl group having 1 to 4 carbon atoms, preferably hydrogen; each $R_{10}$, $R_{11}$, and $R_{12}$ is an alkyl group having 1 to 4 carbon atoms, preferably a methyl group; and pharmaceutically acceptable salts thereof.

DETAILED DESCRIPTION OF THE INVENTION

A. Ibuprofen-Aspirin Compounds

The preferred compounds of formula I are the phenolic esters of ibuprofen with salicylic acid or its nontoxic pharmaceutically acceptable salts (i.e., the p-isobutyl hydratropic acid esters of salicylic acid and its nontoxic salts, also called the alpha-methyl-4-(2-methylpropyl)benzene-acetic acid esters of salicylic acid and its nontoxic salts).

Compounds of formula I within the present invention include but are not limited to p-isobutyl hydratropoyl salicylic acid and its sodium, potassium, lithium, calcium and ammonium salts, m-isobutyl hydratropoyl salicylic acid and its sodium, potassium, lithium, ammonium and calcium salts, p-isoamyl hydratropoyl salicylic acid and its sodium, potassium, lithium, ammonium and calcium salts, p-sec-butyl hydratropoyl salicylic acid and its sodium, potassium, lithium, ammonium and calcium salts, p-n-butyl hydratropoyl salicylic acid and its sodium, potassium, lithium, calcium and ammonium salts, p-isohexyl hydratropoyl salicylic acid and its sodium, potassium, lithium, ammonium and calcium salts, p-tert-butyl hydratropoyl salicylic acid and its sodium, potassium, lithium, ammonium and calcium salts, phenyacetoyl salicylic acid and its sodium, potassium, lithium, ammonium and calcium salts, p-isobutylphenylacetoyl salicylic acid and its sodium, potassium, lithium, calcium and ammonium salts, gamma-p-isobutylphenyl valeroyl salicylic acid and its sodium, potassium, lithium, ammonium and calcium salts, delta-p-isobutylphenyl caproyl salicylic acid and its sodium, potassium, lithium, calcium and ammonium salts, alpha-methyl-3-(2-methylpropyl)benzene-acetoyl salicylic acid and its sodium, potassium, lithium, ammonium and calcium salts, alpha-methyl-2-(2-methylpropyl)benzene-acetoyl salicylic acid and its sodium, potassium, lithium, calcium and ammonium salts, 2,4-di(2-methylpropyl)benzene-acetoyl salicylic acid and its sodium, potassium, lithium, calcium and ammonium salts, alpha-methyl-2,4,5-triethylbenzene-acetoyl salicylic acid and its sodium, potassium, lithium, ammonium and calcium salts, as well as the salicylic acid derivatives within formula I of the aralkyl acids disclosed in British Patent Specification 971,700 and U.S. Pat. Nos. 3,228,831 and 3,385,886 (Nicholson et al), issued Jan. 11, 1966 and May 28, 1968. Further compounds within formula I when $R_1$ is benzoyl include, for example, 2-(3-benzoylphenyl)-propionoyl salicylic acid and its sodium, potassium, lithium, calcium and ammonium salts.

The compounds of formula I of the present invention can be used, for example, in treating humans or other mammals, e.g., in veterinary medicine to treat dogs or cats, as an analgesic, as an anti-pyretic and as an anti-inflammatory agent. They can also be used in mammals in the prevention of heart attacks and can be used in treating an aspirin-treatable cancer, e.g., lung cancer, breast cancer, prostate cancer or colon cancer, by administering to a mammal in need of such treatment an amount sufficient to effect such cancer treatment. The compounds of the present invention, e.g., the ibuprofen esters of salicylic acid, can have longer lasting effectiveness than either ibuprofen or aspirin alone or in admixture. One reason for this is that ibuprofen will itself be one of the decomposition products of the esters of the present invention.

The compounds of formula I of the present invention can be made by the methods described in U.S. Pat. No. 5,760,261 (Guttag), issued Jun. 2, 1998, the entire disclosure of which is hereby incorporated by reference. Thus there can be used as the starting materials acyl halides such as p-isobutylhydratropoyl chloride, bromide and iodide. The compounds of formula I can be made using conventional acylation procedures including those used in the art mentioned in U.S. Pat. No. 5,760,261 at col., 3 lines 32–48. There can also be used the procedures shown in Pala, *J. Med Chem.* Vol. 11(4) pages 910–911 and Hrabak, *Chem. Abst.* Vol. 84 page 430 item 16972p (and corresponding Czech patent 158,430) with the modification that there is no need to add hydroquinone as done in Hrabak. There can also be used the procedure described in Maruko, *Chem. Abst.* Vol. 94 page 544 item 46974q. Ester interchange can also be used as described in U.S. Pat. No. 5,760,261.

A typical example of making a compound of formula I of the present invention is as follows: p-isobutylhydratropoyl chloride (0.06 mole) is added gradually to an ice-cooled stirred solution of salicylic acid (0.06 mole) in anhydrous ether (100 ml). The mixture is then stirred for about 15 hours at room temperature and then refluxed for 5 hours. The suspension is cooled and filtered and the solution is washed and dried and the solvent is removed.

The dosage of the compounds of formula I of the present invention can be readily determined by one of ordinary skill in the art and can range from 1 to 10 milligrams or even up to 1 gram. Thus there can be used, for example, dosages of 0.5 to 10 mg/kg, e.g., 5 to 7 mg/kg body weight. Commonly tablets can contain 325 mg.

Typical formulations can be those set forth in U.S. Pat. No. 5,760,261 (see col. 4 line 60 to col. 5 line 24) by substituting p-isobutylhydratropoyl salicylic acid for the acryloyl salicylic acid of this patent.

As a first example, a capsule can be prepared by mixing about 800 grams of a compound of formula I of the present invention with about 175 grams of microcrystalline cellulose, about 315 grams of lactose and about 10 grams of magnesium stearate. About 100 mg of the mixture is, in each case, is filled into solid size 3 gelatin capsules. One capsule contains about 65 mg of active material, such as the alpha-methyl-4-(2-methylpropyl)benzene-acetic acid ester of salicylic acid.

As a second example, a tablet can be prepared comprising about 1 to 1000 mg, usually about 20 to 700 mg, of active material together with microcrystalline cellulose, starch and magnesium stearate. A typical formula for such a tablet is as follows:

| | |
|---|---|
| Microcrystalline cellulose | 130 mg |
| Modified starch | 20 mg |
| Magnesium stearate | 5.5 mg |
| Polyvinylpyrrolidone | 22 mg |
| Stearic acid | 30 mg |
| p-isobutyl hydratropic acid ester of salicylic acid | 500 mg |

As a third example, a tablet can be prepared as follows: about 13 kg of p-isobutyl hydratropic acid ester of salicylic acid. About 5 kg lactose and about 3 kg of microcrystalline cellulose are mixed with about 0.3 kg of polyvinylpyrrolidone in about 12 kg of water. There is added about 3.45 kg of microcrystalline cellulose, about 2 kg corn starch, about 0.05 kg of highly dispersed silica and about 0.2 kg magnesium silicate. The mixture is molded into a tablet weighing about 220 mg and having a 9 mm diameter and a radius of curvature of about 13.5°. Each tablet contains about 130 mg of active material.

B. Hydroxymethylacylfulvene Analog Compounds

The compounds of formula II are the ester analogues of hydroxymethylacylfulvene (HMAF) reported in *Chem. & Eng. News* (Feb. 10, 1997), pages 7–8. The compounds of formula II can be in the form of pharmaceutically acceptable salts, including organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts can also be formed, including hydrochloride, sulfate, nitrate, bicarbonate, and carbonate salts. Pharmaceutically acceptable salts can be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of formula II can be made from alkenoic acids, alkadienoic acids, alkatrienoic acids, alkatraenoic acids, alkahexaenoic acids, phenoxyalkanoic acids, e.g., phenoxyacetic acid and phenoxypropionic acid and their ring halogenated derivatives such as chlorophenoxyacetic acid (any of the ortho, meta or para isomers), bromophenoxyacetic acid (e.g., para-bromphenoxyacetic acid), orthofluorophenoxyacetic acid, para-iodophenoxyacetic acid, dihalophenoxyacetic acids (e.g., 2,4-dichlorophenoxyacetic acid, 2,4-dibromophenoxyacetic acid, 2,4-difluorophenoxyacetic acid, and 2,4-diiodophenoxyacetic acid), trihalophenoxyacetic acids (e.g., 2,4,5-trichlorophenoxyacetic acid) and the like. The acids from which the esters are made have at least 3 carbon atoms, typically from 3 to 30 carbon atoms, more typically from 3 to 24 carbon atoms.

Compounds of formula II can also be made as esters of alkylidene bis-phenoxyalkanoic acids as shown in U.S. Pat. No. 3,630,715 (Guttag), issued Dec. 28, 1971, e.g., within the formula in the ABSTRACT or within Formula (A) or Formula (B) of claim 1, the entire disclosure of which is hereby incorporated by reference and relied upon. Examples of such acids include, for example, 4,4'-isopropylidene bis-phenoxyacetic acid, 4,4'-isopropylidene bis-(2,6-dichlorophenoxyacetic acid), 4,4'-isopropylidene bis-(2,6-dibromophenoxyacetic acid), 4,4'-isopropylidene bis-(2,6-difluorophenoxyacetic acid) and the like. When the dibasic acids of U.S. Pat. No. 3,630,715 are used to make the novel esters of the present invention then the products can either have a free acid group or can be diesterified (i.e., as mono- or diesters). When they have a free (unesterified) acid group (i.e., an COOY group), this can be left as such (Y is hydrogen) or can be converted to a salt forming element or group, e.g., Y is a sodium, potassium, calcium, magnesium, barium, radium or ammonium salt.

An important significance of the use of the phenoxyacetic acid (and phenoxypropionic acid) esters previously described is that they are herbicides and/or insecticides and hence have toxicity properties which can make them more effective against cancer cells with possibly less damage to normal cells. This could especially be true if these compounds are used in lower dosages than the esters which are not herbicides or insecticides. Those compounds of formula derived from phenoxyacetic acids can also be used as herbicides, e.g., when used within the dosage ranges set forth in U.S. Pat. No. 3,630,715, which is incorporated by reference.

Compounds of formula II formed as esters of ethylenically unsaturated carboxylic acids can be especially suitable, e.g., esters of acrylic acid, methacrylic acid, crotonic acid, maleic acid, palmitoleic acid, oleic acid, linoleic acid, linolenic acid, ricinoleic acid, erucic acid, docosahexaenoic acid (DHA), arachidonic acid and brassidic acid. (DHA occurs in shellfish and other animals as shown, for example, in the article from Prouix, "Scientists Debate Change in Infant Formula," *The Washington Post* Health Section (Mar. 4, 1997), page 19, the entire disclosure of which is hereby incorporated by reference and relied upon).

Compounds of formula II can be formed as esters of ethylenically unsaturated open chain terpene (and related) acid asters, e.g., esters of the terpene acids disclosed in Pala, *J. Med Chem.* Vol. 11(4) pages 910–911, the entire disclosure of which is hereby incorporated by reference and relied upon, including, for example, the esters of 4-methyl-3-pentenoic acid, 5-methyl-4-hexenoic acid, geranic acid, citronellic acid, homogeranic acid, geranylacetic acid, farnesic acid, homofarnesic acid and farnesylacetic acid.

The ester compounds of formula II can be made by methods known to those in the art for esterifying or interesterifying phenolics with fatty acids, fatty acid anhydrides or esters. For example, the ester compounds of formula II can be made by methods disclosed in U.S. Pat. No. 5,910,511 (Guttag), issued Jun. 8, 1999. Esterifying methods are shown on column 3 line 31 to column 4 line 13 of the referenced patent and the patents cited therein. The entire disclosure of U.S. Pat. No. 5,910,511 and of the patents cited therein are hereby incorporated by reference and relied upon. The ester compounds of formula II can also be made by the esterifying procedure shown in Czech patent 158,430 (the entire disclosure of which is hereby incorporated by reference and relied upon. The ester compounds of formula II can also be made by esterifying procedures set forth in the above mentioned Pala article, as well as the esterifying procedures mentioned in U.S. Pat. No. 3,630,715, e.g. in Example 2. In addition, the ester compounds of formula II can be made by esterifying procedures set forth in U.S. Pat. No. 3,220,960 (Wichterle et al), issued Nov. 30, 1965, which is incorporated by reference, and can also be polymerized according to the procedures set forth in U.S. Pat. No. 3,220,960.

Hydroxymethylacylfluvene (HMAF) as the alcohol is the preferred starting material to make the esters of formula II. See U.S. Pat. No. 5,439,936 (Kelner et al), issued Aug. 8, 1995; U.S. Pat. No. 5,523,490 (Kelner et al), issued Jun. 4, 1996; U.S. Pat. No. 5,563,176 (Kelner et al), issued Oct. 8, 1996; U.S. Pat. No. 6,025,328 (McMorris et al), issued Feb. 15, 2000); and U.S. Pat. No. 6,069,283 (McMorris et al), issued May 30, 2000, all of which are incorporated by reference. The esters of HMFA according to formula II can be made, for example, by the method shown in U.S. Pat. No. 5,563,176, as well as the procedures shown in U.S. Pat. No. 6,069,283, both of which are incorporated by reference.

The ester compounds of formula II are useful as antitumor drugs, e.g., in treating breast cancer, lung cancer, colon cancer and prostate cancer, having activity as does HMAF. The dosage ranges for tumor and related treatments can be the same as or similar to those set forth at column 13, lines 22–42 of U.S. Pat. No. 6,025,328 and at column 6, line 40 to column 8, line 8 of U.S. Pat. No. 5,563,176, both of which are incorporated by reference. For example, the ester compounds of formula II can conveniently be administered in unit dosage form; for example, containing 5 to 1000 mg, conveniently 10 to 750 mg, most conveniently, 50 to 500 mg of active ingredient per unit dosage form. Ideally, the active ingredient should be administered to achieve peak plasma concentrations of the active compound of from about 0.5 to about 75 $\mu$M, preferably from about 1 to about 50 $\mu$M, most preferably from about 2 to about 30 $\mu$M. This can be achieved, for example, by the intravenous injection of a 0.05 to 5% solution of the active ingredient, optionally in saline, or orally administered as a bolus containing about 1–100 mg of the active ingredient. Desirable blood levels can be maintained by continuous infusion to provide about 0.01–5.0 mg/kg/hr or by intermittent infusions containing about 0.4–15 mg/kg of the active ingredient(s). The desired dose can conveniently be presented in a single dose or as divided doses administered at appropriate intervals, for example, as two, three, four or more sub-doses per day.

The DHA esters of HMAF according to formula II also can be used in place of DHA for the uses mentioned in the Health Section article, e.g., in infant formulas. Additionally the HMAF esters of other long chain unsaturated fatty acids such as those of linoleic acid, linolenic acid, arachidonic acid and erucic acid can also be used in place of DHA for the uses mentioned in the Health Section article.

The ester compounds of formula II derived from phenoxyalkanoic acids can also be useful as herbicides, e.g., within the dosage ranges set forth in U.S. Pat. No. 3,630,715.

The unsaturated esters of formula II can also be used to form polymers in the same manner as described in U.S. Pat. No. 5,910,511, e.g., column 5 lines 27–38 and Czech patent 158,430. These polymers can be formed into containers, e.g. cups, made into contact lenses or as implants.

C. Pharmaceutical Compositions

The pharmaceutical compositions of the present invention can comprise as the active ingredient at least one compound of formula I or formula II. The composition can be present in any conventional unit dosage form, for example as a pill, capsule, tablet, gel tablet or even liquid form. The composition can further comprise other pharmaceutically active materials, for example, aspirin, ibuprofen, acetaminophen, streptokinase, urokinase or tissue plasminogen activator (tPA). The composition of the invention can also include a pharmaceutically acceptable carrier or diluent, see for example, U.S. Pat. No. 4,643,995 (Engel et al), issued Feb. 17, 1987, especially at col. 13 line 35 to col. 15 line 54, which is incorporated by reference.

The pharmaceutical compositions of the present invention can be administered to a mammalian host, such as a human patient in a variety of dosage forms adapted to the chosen route of administration, i.e., orally or parenterally, by intravenous, intramuscular, topical or subcutaneous routes. See, for example, column 11, line 8, to column 12, line 67 of U.S. Pat. No. 6,025,328, which is incorporated by reference. The active compounds of formula I or II can be systemically administered, e.g., orally, in combination with a pharmaceutically acceptable vehicle such as an inert diluent or an assimilable edible carrier. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations can, of course, be varied and can conveniently be from about 2 to about 60% of the weight of a given unit dosage form. The amount of active compound in such therapeutically useful compositions is such that an effective dosage level will be obtained.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

The active compounds of formula I or II can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compounds of formula I or II in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the active compounds of formula I or II can be applied in pure form, e.g., when they are liquids. However, it will generally be desirable to administer them to the skin as compositions or formulations, in combination with a dermatologically acceptable carrier, which can be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

While specific embodiments of the present invention have been described, it will be apparent to those skilled in the art that various modifications thereto can be made without departing from the spirit and scope of the present invention as defined in the appended claims.

What is claimed is:

1. A method for reducing the risk of heart attack comprising administering to a mammal with risk of heart disease an amount sufficient to reduce the risk of heart attack of a compound of formula I:

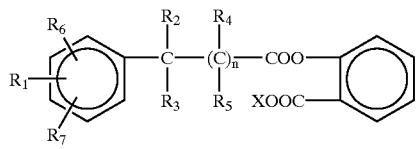

wherein $R_1$ is hydrogen, benzoyl or alkyl, $R_2$ and $R_3$ are hydrogen or lower alkyl, n is zero or a small integer, $R_4$ and $R_5$ are hydrogen or lower alkyl, $R_6$ and $R_7$ are hydrogen or alkyl, and X is hydrogen or a pharmaceutically acceptable salt forming metal or group.

2. The method according to claim 1 wherein $R_6$ and $R_7$ are hydrogen.

3. The method according to claim 2 wherein n is zero and wherein $R_1$ is alkyl, $R_2$ is hydrogen and $R_3$ is methyl.

4. The method according to claim 3 wherein $R_1$ is in the para position and is isobutyl.

5. The method according to claim 1 wherein $R_1$ is benzoyl.

6. The method according to claim 1 wherein $R_1$ is hydrogen or alkyl.

7. The method according to claim 6 wherein $R_2$ and $R_3$ are hydrogen or lower alkyl of 1 to 6 carbon atoms.

8. The method according to claim 7 wherein n is 1, 2 or 3.

9. The method according to claim 6 wherein $R_1$ is branched chain alkyl.

10. A method for treating an aspirin-treatable cancer by administering to a mammal in need of such treatment an amount sufficient to effect such cancer treatment of a compound of formula I:

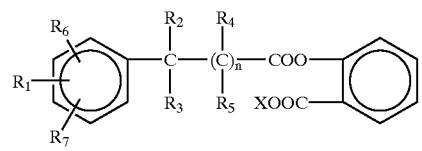

wherein $R_1$ is hydrogen, benzoyl or alkyl, $R_2$ and $R_3$ are hydrogen or lower alkyl, n is zero or a small integer, $R_4$ and $R_5$ are hydrogen or lower alkyl, $R_6$ and $R_7$ are hydrogen or alkyl, and X is hydrogen or a pharmaceutically acceptable salt forming metal or group.

11. The method according to claim 10 wherein $R_6$ and $R_7$ are hydrogen.

12. The method according to claim 11 wherein n is zero and wherein $R_1$ is alkyl, $R_2$ is hydrogen and $R_3$ is methyl.

13. The method according to claim 12 wherein $R_1$ is hydrogen or alkyl.

14. The method according to claim 13 wherein $R_2$ and $R_3$ are hydrogen or lower alkyl of 1 to 6 carbon atoms.

15. The method according to claim 14 wherein n is 1, 2 or 3.

16. The method according to claim 10 wherein $R_1$ is in the para position and is isobutyl.

17. The method according to claim 10 wherein $R_1$ is benzoyl.

18. The method according to claim 10 wherein the mammal is a human.

* * * * *